United States Patent [19]

Haruta

[11] 4,246,773
[45] Jan. 27, 1981

[54] COMBUSTION PROPERTY OF GAS MEASURING APPARATUS

[75] Inventor: Masao Haruta, Osaka, Japan

[73] Assignee: Osaka Gas Company Ltd., Osaka, Japan

[21] Appl. No.: 22,357

[22] Filed: Mar. 20, 1979

[30] Foreign Application Priority Data

Mar. 31, 1978 [JP] Japan .................................. 53-38707
Mar. 31, 1978 [JP] Japan .................................. 53-38708
Jun. 26, 1978 [JP] Japan .................................. 53-77667

[51] Int. Cl.³ ........................................... G01N 29/02
[52] U.S. Cl. ..................................................... 73/24
[58] Field of Search ................. 73/24; 137/88, 91, 551

[56] References Cited

U.S. PATENT DOCUMENTS

| | | | |
|---|---|---|---|
| 2,952,153 | 9/1960 | Robinson | 73/24 |
| 3,381,520 | 5/1968 | Bourquard et al. | 73/24 |
| 3,789,655 | 2/1974 | Passeri | 73/24 |
| 3,848,457 | 11/1974 | Behymer | 73/24 |

OTHER PUBLICATIONS

"Experimental Method of Natural Gas," Toru Ogawa, pp. 124-126, Aug. 10, 1945.

*Primary Examiner*—Stephen A. Kreitman
*Attorney, Agent, or Firm*—Wenderoth, Lind & Ponack

[57] ABSTRACT

The present invention relates to apparatus for measuring calorific value and Wobbe index of gas by determining the specific gravity of the gas, and apparatus for controlling the calorific value of the gas in accordance with the specific gravity. The specific gravity of the gas is related to the sonic speed in the gas which is determined by means of electric equipment. The electric equipment contains a pair of acoustic tubes, in one of which is contained gas being measured, and in the other of which is contained standard gas. Each of the acoustic tubes is provided at opposite ends thereof with a microphone and a speaker, and a pair of amplifiers, one each associated with a respective microphone and speaker. Howling occurs in each acoustic tube. Consequently a signal having a beat frequency is obtained by mixing and detecting the outputs from the amplifiers, and the beat frequency is representative of the specific gravity of the gas being measured.

4 Claims, 3 Drawing Figures

COMBUSTION PROPERTY OF GAS MEASURING APPARATUS

BACKGROUND OF THE INVENTION

1. Field of the Invention

The present invention relates to an apparatus for measuring the combustion property of gas, and more particularly is concerned with electric equipment for evaluating calorific value and Wobbe index of gas being measured. The invention further relates to an apparatus for controlling the calorific value of mixed gas.

2. Description of the Prior Art

Gross calorific value and Wobbe index of gas are known as important factors indicating combustion properties of gas. Wobbe index WI is defined as follows:

$$WI = \frac{Q}{\sqrt{\gamma}} \quad (1)$$

Where Q is gross calorific value of the gas being measured, and $\gamma$ is the specific gravity of the gas being measured. It is understood, therefore, that the gross calorific value Q and specific gravity $\gamma$ are required in order to determine Wobbe index WI.

In the past, certain disadvantages have been indigenous to the technique of measurement of the gross calorific value. For example, the gas being measured is mixed with air for combustion to burn continuously under a given condition. Resultantly produced gas is taken into a heat exchanger in which evolved combustion heat is absorbed into cooling water running therethrough at a fixed flow rate. In such heat exchanger technique, the temperatures and flow rates of the gas being measured, the air for combustion and the cooling water, as well as ambient temperatures, should be kept constant, and such temperatures, flow rates and ambient temperatures are measured individually. Gross calorific value is then obtained by calculating those measured values. Such prior art generally suffers the disadvantage of requiring considerable time for the measurements to be conducted. Also the accuracies of the measurements so obtained are affected by variations in ambient conditions under which such measurements are conducted.

Another prior art aspect of gross calorific value control of mixed gas employs the above-mentioned technique wherein the gross calorific value measured is compared with a target value when they disagree, the gross calorific value of the mixed gas is controlled to coincide with the target value by changing the mixing ratio of gas components which compose the mixed gas. In this technique, therefore, it is extremely difficult to control the gross calorific value of the mixed gas accurately and quickly.

In brief, therefore, prior art systems for measurement of gas combustion properties have suffered from limited accuracy, slow speed and high man-hour costs.

SUMMARY OF THE INVENTION

By means of the concept of the invention, the above-mentioned shortcomings of the prior art are avoided and there is provided apparatus for measuring gas combustion properties with increased accuracy, faster speed and involving lesser costs in man-hours, and there is provided further apparatus for controlling a gas calorific value accurately and quickly.

In accordance with the invention, there is provided means for producing an electrical output signal which corresponds to the sonic speed in the gas being measured. The sonic speed is related to specific gravity, gross calorific value and Wobbe index of the gas. There are also provided means responsive to the output signal from the electrical output signal producing means for determining the gross calorific value and Wobbe index. Gross calorific value of a gas mixture is controlled by determination of the specific gravity which corresponds to the mixing ratio of gas components of which the mixed gas consists.

By means of such arrangement, errors due to ambient conditions in the continuous measuring operations are avoided. Also the use of an electric means for measuring sonic speed automatically provides increased data of continuous gross calorific value and Wobbe index in less time than that required to manually sample a limited number of individual measurements of the temperatures and flow rates of the gases and the cooling water, as in the above-mentioned prior art system, and also allows such measurement to be conducted in a minimum amount of man-hour costs. Also, in accordance with the invention, besides gross calorific value and Wobbe index, net calorific value of gas is capable of being determined. The gas being measured may be (1) mixed gas which consists of plural gas components of a homologous series of hydrocarbons, or (2) a gas mixture which consists of air and a single hydrocarbon.

Accordingly, it is an object of this invention to provide an improved apparatus for measuring the combustion property of gas.

It is another object of the invention to provide such apparatus of improved accuracy.

It is another object to provide such apparatus requiring fewer man-hours to determine the combustion property of gas.

It is another object of the invention to provide improved apparatus for controlling the calorific value of gas.

It is still another object of the invention to provide such apparatus of improved accuracy and of high speed.

BRIEF DESCRIPTION OF THE DRAWINGS

These and other objects of the invention will become apparent from the following description, taken together with the accompanying drawings, in which.

In the figures, like reference characters refer to like parts.

DETAILED DESCRIPTION OF THE PREFERRED EMBODIMENTS

Figure 1:
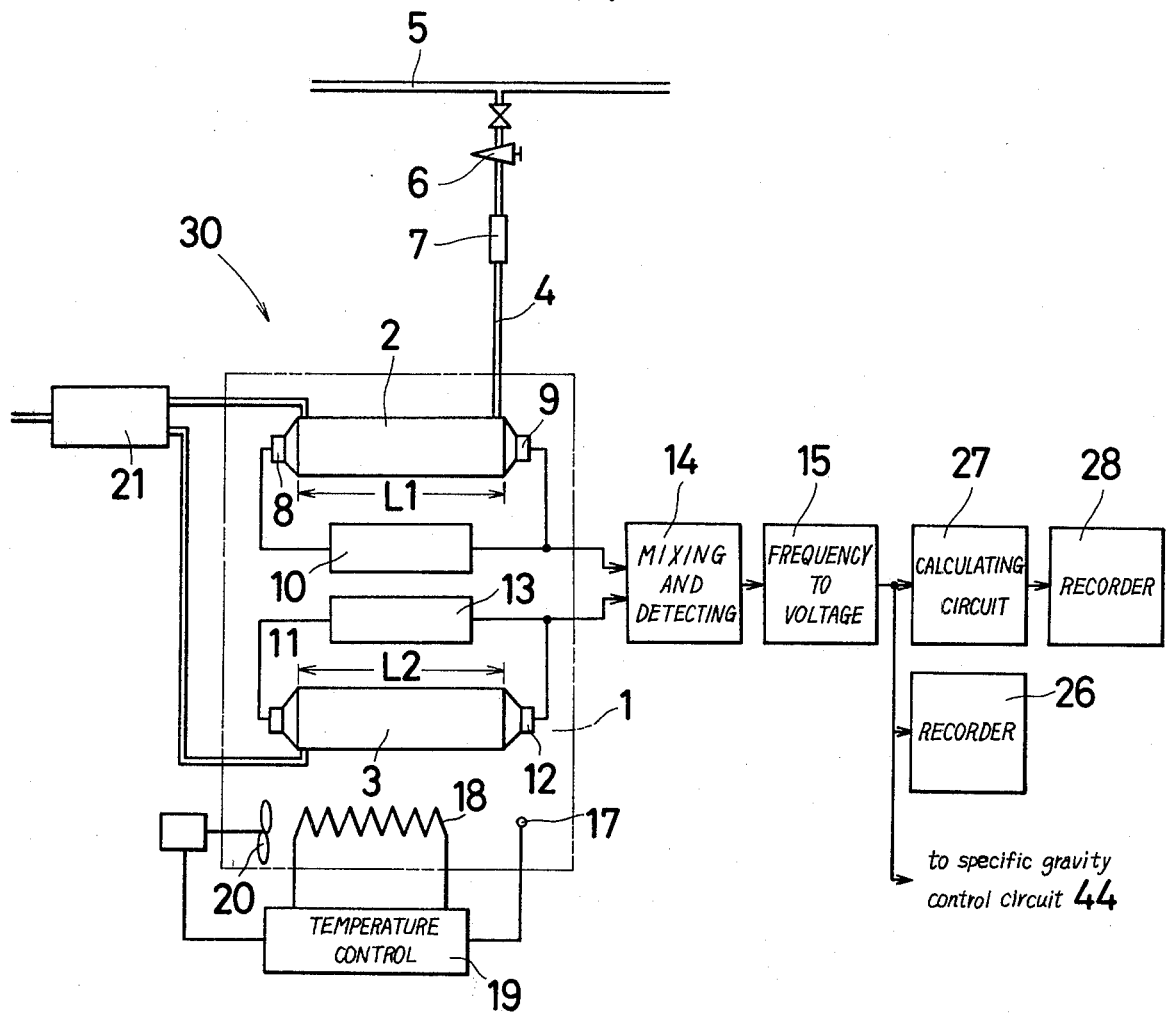
FIG. 1 is a block diagram of a system illustrating one aspect of the invention.

Referring now to FIG. 1, there is illustrated a system 30 for measuring gross calorific value and Wobbe index of town gas which is vaporized from liquefied natural gas (LNG). This town gas is mixed gas which consists of plural paraffinic hydrocarbons $C_nH_{2n+2}$. A pair of acoustic tubes 2 and 3 are placed in a thermostatic bath 1. The gas to be measured is introduced into one acoustic tube 2 through a passage 4 which branches off from a gas pipe 5. A reducing valve 6 and a flow meter 7 are provided in the passage 4. In the other acoustic tube 3, is contained standard gas which is natural gas having similar gas components. The acoustic tubes 2 and 3 are substantially of the same dimensions and construction. At opposite ends of the acoustic tube 2 are installed a microphone 8 and a speaker 9 respectively. The electrical output signal from the microphone 8 is fed to the input of an amplifier 10, the output from which is coupled to the speaker 9. The length of the acoustic tube 2, that is the distance L1 between the microphone 8 and the speaker 9, is selected so that howling occurs in the acoustic tube 2 at a frequency f1 corresponding to the distance L1 and sonic speed u1 in the gas being measured. There are provided a microphone 11, a speaker 12, and an amplifier 13 associated with the other acoustic tube 3 in a manner similar to the acoustic tube 2. The distance L2 between the microphone 11 and the speaker 12 is selected to be equal to L1 (L1=L2). The acoustic standing wave corresponding to the distance L2 and sonic speed u2 of the standard gas in the acoustic tube 3 howls at a frequency of f2.

A temperature detecting device 17 and a heater 18 are placed in the thermostatic bath 1. A temperature control circuit 19 is responsively coupled to the temperature detecting device 17, and energizes the heater 18, whereby the atmospheric temperature in the thermostatic bath 1 is kept constant. A fan 20 stirs the air in the thermostatic bath 1.

Pressure p1 in the acoustic tube 2 and pressure p2 in the acoustic tube 3 are controlled with the same pressure by a pressure compensator 21 (p1=p2). The relation between the sonic speed u in the gas and the gas density $\rho$ is represented by equation (2).

$$u^2 = 101.32R \frac{1 + \alpha t}{\rho} \text{ (m/sec)}^2 \qquad (2)$$

where,
t: gas temperature
$\rho$: density at 0° C.
$\alpha$: temperature coefficient
R: specific heat ratio of gas
(R=constant-pressure specific heat Cp/constant-volume specific heat $C_v$)

Meanwhile, the gas being measured in the acoustic tube 2 and the standard gas in the acoustic tube 3 are related with each other as represented by equation (3). In equation (3), terms affixed with number "1" refer to the gas being measured, and those with "2" refer to the standard gas.

$$\frac{u1^2}{u2^2} = \frac{R1}{R2} \cdot \frac{1 + \alpha \cdot t1 \cdot \rho1}{1 + \alpha \cdot t2 \cdot \rho1} \qquad (3)$$

Hence, in the acoustic tube 2, the relation shown in equation (4) is established among sonic speed u1, frequency f1 and wavelength $\lambda1$.

$$u1 = f1 \cdot \lambda1 \qquad (4)$$

In the particular embodiment as shown, there is the acoustic standing wave resonating with the acoustic tube 2, and the distance L1 is selected according to the following equation (5):

$$\lambda1 = 4 \cdot L1 \qquad (5)$$

Since the gas components of the gas being measured are similar to those of the standard gas and the pressure of both gases are equal to each other, it follows that R1$\approx$R2. Also t1=t2. Therefore, according to equations (3) through (5), equations (6) and (7) are established as follows:

$$\frac{\rho 1}{\rho 2} = \left(\frac{f1}{f2}\right)^2 \qquad (6)$$

$$\therefore \rho 1 = \rho 2 \left(\frac{\Delta f}{f2} + 1\right)^2 \qquad (7)$$

Density $\rho2$ and frequency f2 of the standard gas are known.

A mixing and detecting circuit 14 is responsively coupled to the outputs from both of the amplifiers 10 and 13, and provides the output signal having a beat frequency $\Delta f$. It will be understood, therefore, that the output from the mixing and detecting circuit 14 is employed to determine density $\rho1$ of the gas being measured by means of the relationship (7).

The relation between the gas being measured and air with respect to specific gravity $\gamma$ and density $\rho1$ is represented as follows:

$$\gamma = \rho 1/\text{density of air} \qquad (8)$$

The inventor of the present invention has discovered that the specific gravity $\gamma$ is related to the gross calorific value Q of the gas being measured. In the case where the gas being measured is mixed gas consisting of six gas components of a methane homologue $C_nH_{2n+2}$, and the mixing ratios of the components are shown in TABLE 1 by volume, specific gravity $\gamma$ and gross calorific value Q may be calculated as follows:

TABLE 1

| Gas component | CH$_4$ | C$_2$H$_6$ | C$_3$H$_8$ | iso-C$_4$H$_{10}$ | n-C$_4$H$_{10}$ | iso-C$_5$H$_{12}$ |
|---|---|---|---|---|---|---|
| Specific gravity $\gamma$ (air = 1) | 0.554 | 1.038 | 1.522 | 2.006 | 2.006 | 2.491 |
| Gross calorific value Q (kcal/Nm$^3$) | 9530 | 16820 | 24320 | 32010 | 32010 | 37670 |
| Volume ratio in the gas being measured (%) | 88.34 | 6.51 | 3.54 | 0.69 | 0.84 | 0.08 |

Specific gravity $\gamma$ of the gas being measured (9)
= 0.554 × 0.8834 + 1.038 × 0.0651 + 1.522 × 0.0354
+ 2.006 × 0.0069 + 2.006 × 0.0084 + 2.491 × 0.0008
= 0.643

Figure 2:
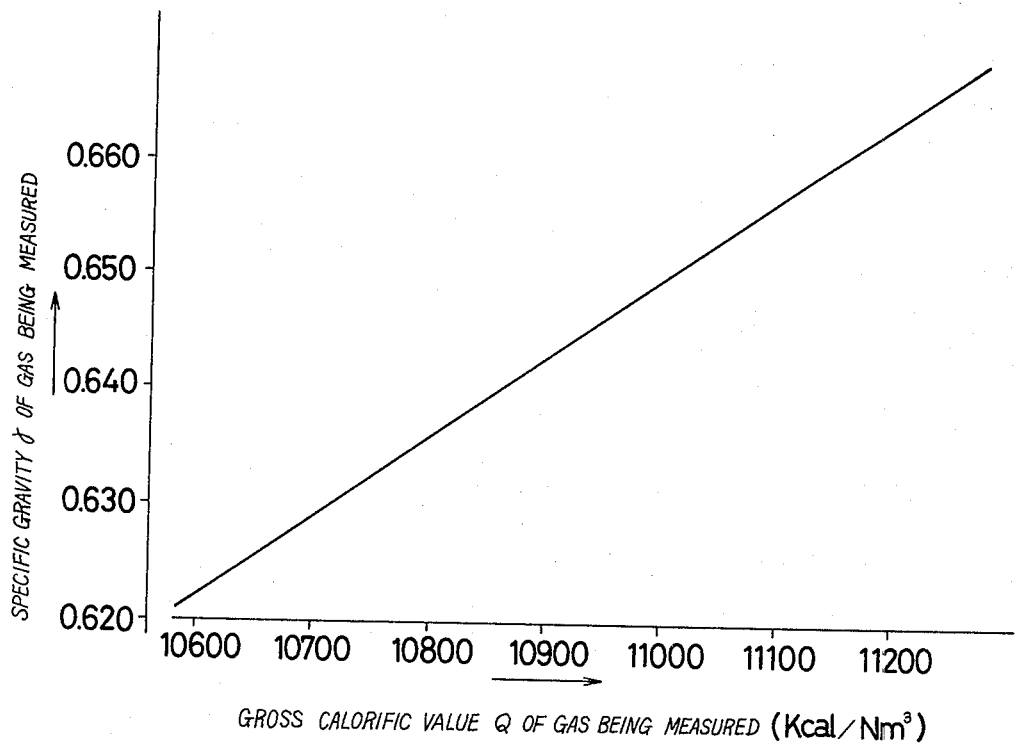
FIG. 2 is an illustration of the relation between specific gravity $\gamma$ and gross calorific value Q of the gas being measured which is obtained by the invention.

Gross calorific value Q (10)
= 9530 × 0.8834 + 16820 × 0.0651 + 24320 × 0.0354
+ 32010 × 0.0069 + 32010 × 0.0084 + 37670 × 0.0008
= 10895 Kcal/Nm$^3$ Specific gravity $\gamma$ and gross calorific value Q of the gas being measured depend on the volume ratio of each gas component of which the methane homologue gas consists. It will be seen that by analogy with the equations (9) and (10), specific gravity $\gamma$ and gross calorific value Q of further mixed gases each having different ratios of the gas components of metane homologue are plotted in FIG. 2. Therefore gross calorific value Q is found in FIG. 2 by calculation of density $\rho1$, and thus specific gravity $\gamma$ in accordance with the equations (7) and (8). In this manner, Wobbe index WI is obtained by the equation (1).

Referring again to FIG. 1, there is provided a frequency-voltage converter 15 responsive to the output from the mixing and detecting circuit 14 having the beat frequency Δf for providing an output having a voltage value corresponding to the beat frequency Δf and thus density ρ1 and gross calorific value Q of the gas being measured.

A recorder 26 responsive to the output from the frequency-voltage converter 15 records and displays the gross calorific value Q. A calculating circuit 27 responds to the output from the frequency-voltage converter 15 and calculates according to the equation (1) to supply an output to the recorder 28 for recording and displaying Wobbe index WI.

Figure 3:
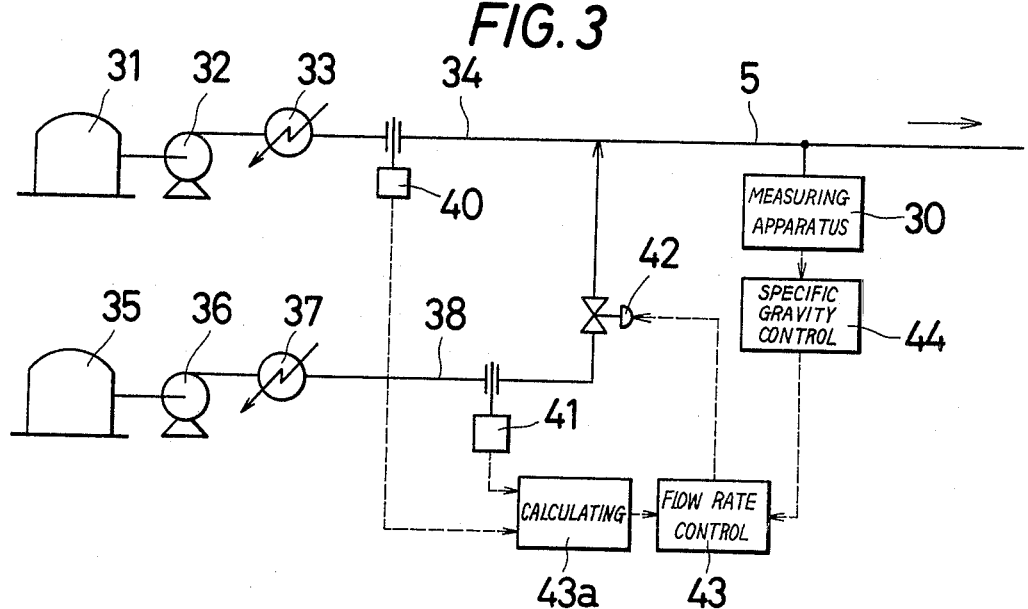
FIG. 3 is a further block diagram according to the invention, which includes apparatus shown in FIG. 1.

Referring now to FIG. 3, there is illustrated calorific value controlling apparatus for maintaining the gross calorific value of the town gas at a predetermined value and utilizing the above-mentioned apparatus shown in FIG. 1. In order to stabilize the gross calorific value of the town gas, natural gas vaporized from liquefied natural gas and a slight quantity of propane or butane are blended together. Since the natural gas vaporized from liquefied natural gas has a slightly smaller amount of gross calorific value than the target value of 11000 kcal/Nm$^3$, propane or butane is blended to adjust the gross calorific value to be suitable as the town gas. Liquefied natural gas is stored in a tank 31. This liquefied natural gas is sent into a vaporizer 33 by a pump 32 to be vaporized into natural gas, which is then led into a pipe 34. On the other hand, liquefied propane or butane is stored in a tank 35, which is pumped by 36 into a vaporizer 37 and is mixed into the pipe 34 of natural gas by way of a pipe 38. The mixture of natural gas from the pipe 34 and propane or butane from pipe 38 will be transferred through the gas pipe 5 as the town gas. Flow meters 40 and 41 are provided in the pipe 34 and 38 respectively, and a flow control valve 42 is installed in the pipe 38. The outputs from these flow meters 40 and 41 are fed into a calculating circuit 43a. The calculating circuit 43a calculates and supplies an output representative of flow rate of the gases in the pipes 34 and 38 to a flow rate control circuit 43. There is also provided the apparatus 30 shown in FIG. 1 associated with the gas pipe 5. A specific gravity control circuit 44 receives the output from the frequency-voltage converter 15 which corresponds to the specific gravity of the town gas flowing in the gas pipe 5, and provides an output indicative of the deviation between specific gravity of the town gas in the gas pipe 5 and the predetermined specific gravity which corresponds to the target value of gross calorific value. The flow rate control circuit 43 responds to the output from the calculating circuit 43a and the output from the specific gravity control circuit 44, and controls the flow control valve 42 so that the flow rate due to the flow meters 40 and 41 coincides with the predetermined flow rate value. Consequently the specific gravity and obtained gross calorific value of the town gas flowing in the gas pipe 5 can be always kept precisely constant.

Although the invention has been described and illustrated in detail, it is to be clearly understood that the same is by way of illustration and example only and is not to be taken by way of limitation, the spirit and scope of the invention being limited only by the terms of the appended claims.

What is claimed is:

1. An apparatus for measuring gross calorific value of a gas to be measured and consisting of a mixed gas which consists of plural gas components of a homologous series of hydrocarbons, said apparatus comprising:

first and second totally separate and isolated acoustic tubes;

means for introducing into said first acoustic tube, from a suitable source, said gas to be measured, said suitable source of said gas to be measured comprising a gas supply pipe, a first supply of a mixed gas consisting of plural gas components of a homologous series of hydrocarbons, and first pipe means connecting said first supply to said gas supply pipe;

means for introducing into said second acoustic tube, from a source isolated and separate from and having no communication with said source of gas to be measured, a standard gas totally separate and isolated from said gas to be measured and of a known gross calorific value, said standard gas consisting of plural gas components of a homologous series of hydrocarbons;

said first acoustic tube having associated therewith first microphone means, first speaker means and first amplifier means for generating a first frequency signal representative of said gross calorific value of said gas to be measured;

said second acoustic tube having associated therewith second microphone means, second speaker means and second amplifier means for generating a second frequency signal representative of said known gross calorific value of said standard gas;

mixing and detecting circuit means for receiving said first and second frequency signals from said first and second amplifier means, respectively, and for generating an output signal having a beat frequency representative of a differential between said first and second frequency signals;

frequency voltage converter means for receiving said output signal from said mixing and detecting circuit means and for generating a voltage output signal proportional to said beat frequency and representative of said gross calorific value of said gas to be measured; and means for maintaining the gross calorific value of said gas to be measured, in said suitable source thereof, at a predetermined value, said maintaining means comprising a second supply of at least one gas component of said homologous series of hydrocarbons, the calorific value of said mixed gas from said first supply being different from the calorific value of said at least one gas component from said second supply, second pipe means connecting said second supply to said gas supply pipe, first and second flow meters in said first and second pipe means, respectively, for measuring the flows therethrough, a flow control valve in said second pipe means for regulating the quantity of said at least one gas component supplied to said gas supply pipe, calculating means connected to said first and second flow meters for producing a flow output representative of the flows through said first and second pipe means, control means connected to said frequency voltage converter means for receiving therefrom said voltage output signal and for generating a difference output indicative of any deviation between said gross calorific value of said gas in said gas supply pipe and said predetermined value, and flow rate control means for receiving said flow output from said calculating means and said difference output from said control means and connected to said flow control valve for controlling said flow control valve to adjust the quantity of said at least one gas component supplied to said gas supply pipe and to thereby adjust the gross calorific value of said gas in said gas supply pipe to said predetermined value.

2. An apparatus as claimed in claim 1, further comprising recording means connected to said frequency voltage converter means for receiving therefrom said voltage output signal and for producing a visual indication of said gross calorific value of said gas to be measured.

3. A process for measuring gross calorific value of a gas to be measured, said process comprising:

providing a source of gas to be measured and consisting of plural gas components of a homologous series of hydrocarbons, said source of said gas to be measured comprising a gas supply pipe, a first supply of a mixed gas consisting of plural gas components of a homologous series of hydrocarbons, and first pipe means supplying said mixed gas from said first supply to said gas supply pipe;

providing a source, isolated and separate from and having no communication with said source of gas to be measured, of a standard gas which is totally separate and isolated from said gas to be measured and which has a known gross calorific value, said standard gas consisting of plural gas components of a homologous series of hydrocarbons;

providing first and second totally separate and isolated acoustic tubes;

introducing said gas to be measured into said first acoustic tube;

introducing said standard gas into said second acoustic tube while at all times maintaining total separation and isolation between said gas to be measured and said standard gas;

generating within said first and second acoustic tubes respective first and second frequency signals representative of said gross calorific value of said gas to be measured and said known gross calorific value of said standard gas, respectively;

mixing said first and second frequency signals and generating an output signal having a beat frequency representative of a difference between said first and second frequency signals;

converting said output signal into a voltage output signal proportional to said beat frequency and representative of said gross calorific value of said gas to be measured; and maintaining the gross calorific value of said gas to be measured, in said source thereof, at a predetermined value, said maintaining comprising providing a second supply of at least one gas component of said homologous series of hydrocarbons, the calorific value of said mixed gas from said first supply being different from the calorific value of said at least one gas component from said second supply, supplying said at least one gas component from said second supply to said gas supply pipe through a second pipe means, measuring the flows through said first and second pipe means by first and second flow meters, respectively, calculating a flow output representative of the flows measured by said first and second flow meters, receiving said voltage output signal and generating a different output indicative of any deviation between said gross calorific value of said gas in said gas supply pipe and said predetermined value, providing a flow control valve in said second pipe means, and controlling said flow control valve in response to said flow output and said difference output to adjust the quantity of said at least one gas component supplied to said gas supply pipe and to thereby adjust the gross calorific value of said gas in said gas supply pipe to said predetermined value.

4. A process as claimed in claim 3, further comprising receiving said voltage output signal and producing therefrom a visual indication of said gross calorific value of said gas to be measured.

* * * * *